(12) United States Patent
García González et al.

(10) Patent No.: US 10,338,022 B2
(45) Date of Patent: Jul. 2, 2019

(54) SENSOR CIRCUIT AND METHOD FOR MEASURING A PHYSICAL OR CHEMICAL QUANTITY

(71) Applicant: ams AG, Unterpremstaetten (AT)

(72) Inventors: José Manuel García González, Paterna (ES); Rafael Serrano Gotarredona, Valencia (ES)

(73) Assignee: ams AG, Unterpremstaetten (AT)

( * ) Notice: Subject to any disclaimer, the term of this patent is extended or adjusted under 35 U.S.C. 154(b) by 43 days.

(21) Appl. No.: 15/572,754

(22) PCT Filed: Mar. 29, 2016

(86) PCT No.: PCT/EP2016/056806
§ 371 (c)(1),
(2) Date: Nov. 8, 2017

(87) PCT Pub. No.: WO2016/180568
PCT Pub. Date: Nov. 17, 2016

(65) Prior Publication Data
US 2018/0136158 A1    May 17, 2018

(30) Foreign Application Priority Data
May 13, 2015 (EP) .................... 15167589

(51) Int. Cl.
G01N 27/22 (2006.01)
G01R 27/26 (2006.01)

(52) U.S. Cl.
CPC ............ *G01N 27/22* (2013.01); *G01R 27/26* (2013.01)

(58) Field of Classification Search
CPC ........ G01N 27/00; G01N 27/02; G01N 27/22; G01R 27/00; G01R 27/02; G01R 27/26;
(Continued)

(56) References Cited

U.S. PATENT DOCUMENTS 5,418,771 A * 5/1995 Kasanuki ................. G01B 7/31
250/310
7,046,129 B2 * 5/2006 Regnet ..................... B60J 10/00
340/426.27

(Continued)

FOREIGN PATENT DOCUMENTS

CA         2255225 A1    6/1999
DE   102006057136 A1   11/2007
(Continued)

OTHER PUBLICATIONS

Rich, A.: "Shielding and Guarding" Analog Dialogue, vol. 17, No. 1, 1983, pp. 8-13.
(Continued)

*Primary Examiner* — Hoi-An D. Nguyen
(74) *Attorney, Agent, or Firm* — Fish & Richardson P.C.

(57) ABSTRACT

A sensor circuit for measuring a physical or chemical quantity comprises a capacitive sensor. A sense and a base electrode of the sensor form a capacitive element with a capacity depending on the quantity. A common electrode of the sensor forms a first and a second parasitic capacitance together with the sense and the base electrode, respectively. The sensor circuit is adapted to store a charge on the capacitive element and to read out the stored charge via the sense electrode. A buffer element is connected between the sense electrode and the common electrode and adapted to drive the common electrode at a voltage applied to the sense electrode.

18 Claims, 2 Drawing Sheets

(58) Field of Classification Search
CPC ........ G01R 27/2605; G01D 5/00; G01D 5/12; G01D 5/14; G01D 5/24; G01D 5/2405; G01D 5/241; G01D 5/2412; G01D 5/2417
USPC ........ 324/600, 649, 658, 660–665, 669–672, 324/686, 688, 689, 323, 347, 357, 358, 324/515
See application file for complete search history.

(56) References Cited

U.S. PATENT DOCUMENTS

| | | | |
|---|---|---|---|
| 8,354,606 B2* | 1/2013 | Yokoyama | H01H 13/705 200/600 |
| 8,490,495 B2* | 7/2013 | Lee | G01L 19/0092 73/715 |
| 8,547,114 B2* | 10/2013 | Kremin | G06F 3/044 324/678 |
| 9,665,231 B2* | 5/2017 | Chang | G06F 3/047 |
| 9,952,716 B2* | 4/2018 | Chang | G06F 3/0416 |
| 2011/0074444 A1* | 3/2011 | Makiranta | G01V 3/088 324/663 |

FOREIGN PATENT DOCUMENTS

| | | |
|---|---|---|
| EP | 1988366 A1 | 11/2008 |
| EP | 2112476 A1 | 10/2009 |

OTHER PUBLICATIONS

Singh, R. R. et al.: "A Compact Parasitic-Insensitive Dual-Frequency Delta-Sigma Modulated CMOS Capacitive Sensor" IEEE Biocas 2010 conference proceedings. pp. 242-245.

* cited by examiner

SENSOR CIRCUIT AND METHOD FOR MEASURING A PHYSICAL OR CHEMICAL QUANTITY

BACKGROUND OF THE INVENTION

The present disclosure relates to a sensor circuit and a method for measuring a physical or chemical quantity, in particular by means of a capacitive sensor. Further, the present disclosure relates to a charge redistribution amplifier circuit, an integrated circuit and a capacitance-to-digital converter circuit comprising such sensor circuit.

Capacitive sensors may be used in many applications to measure physical or chemical quantities as for example humidity, pressure, liquid level, purity or proximity. For achieving a desired or required accuracy, the measurement may require a high resolution and a low noise. For example, parasitic capacitances may affect or reduce an accuracy of the measurement.

Existing approaches may for example reduce a processing speed and/or increase a power consumption, for example by introducing additional measurements.

SUMMARY OF THE INVENTION

The present disclosure provides an improved concept for measuring a physical or chemical quantity by means of a capacitive sensor according to which an influence of parasitic capacitances is reduced or avoided and that overcomes said problems.

According to the improved concept, an influence of parasitic capacitances formed between a sense electrode of a capacitive sensor and a common electrode of the sensor and/or between a base electrode of the sensor and the common electrode is suppressed by driving the common electrode to the same voltage as the sense electrode. Therein, the base and the sense electrode are used for storing a charge on a capacitive element of the sensor formed by the sense electrode and the base electrode. The common electrode corresponds for example to a bottom or a top plate of the parasitic capacitances.

The sense electrode is then used for reading out the charge, which depends on the physical or chemical quantity to be measured.

According to the improved concept a sensor circuit for measuring a physical or chemical quantity is provided. The sensor circuit comprises a buffer element and a capacitive sensor with a sense electrode, a base electrode and a common electrode. The sense electrode and the base electrode together form a capacitive element of the sensor, the capacitive element having a capacity depending on the physical or chemical quantity to be measured.

The common electrode forms a first parasitic capacitance together with the sense electrode and a second parasitic capacitance together with the base electrode. Therein, the sensor is adapted to store a charge on the capacitive element via the sense electrode and the base electrode and to read out the stored charge via the sense electrode.

The buffer element is connected between the sense electrode and the common electrode and adapted to drive the common electrode at a voltage applied to the sense electrode at least during the reading out of the stored charge.

In particular, if a voltage applied to the sense electrode changes, for example during the reading out of the stored charge, the buffer element continuously drives the common electrode to the same voltage that is applied to the sense electrode. That is, when a voltage applied to the sense electrode changes, the voltage to which the common electrode is driven changes, too. Consequently, a charge stored on the first parasitic capacitance remains constant, at least during the reading out of the charge stored on the capacitive element.

According to the advanced concept, the sense electrode and the common electrode are for example virtually shorted. However, by utilizing the buffer element, charge stored on the second parasitic capacitance cannot be transferred to the sense electrode in contrast to an actual shorting of the sense and the common electrode. In this way, the charge stored on the capacitive element may be read out more accurately, in particular without an influence or with a reduced influence from the first and the second parasitic capacitance.

The physical or chemical quantity corresponds for example to at least one of the following: an environmental condition, a pressure, an air pressure, a contact pressure, an acoustic pressure, an ambient pressure, a humidity, an air humidity, a liquid level, a purity, a concentration, a proximity, a distance, and angle, an acceleration.

The capacitance of the capacitive element may for example depend on the quantity in that variations in the quantity lead to variations in a position, an orientation and/or a shape of the sense electrode and/or the base electrode. Alternatively or in addition, variations in the quantity may lead to variations in a permittivity of a dielectric material, for example air, between the sense electrode and the base electrode and thereby change the capacitance.

In some implementations, the first and/or the second parasitic capacitance depend on the physical or chemical quantity to be measured. In alternative implementations, the first and the second parasitic capacitance do not depend on the quantity.

In principle, due to the first and the second parasitic capacitance, a signal generated by the capacitive sensor when the charge being stored on the capacitive element is read out via the sense electrode, may be influenced by the first and/or the second capacitance. According to the improved concept, however, the buffer element drives the common electrode to the same voltage as applied to the sense electrode. Therefore, an influence of the first and the second parasitic capacitance on said signal may be avoided or reduced.

According to some implementations, the common electrode surrounds at least a part of the sense electrode and/or the base electrode.

According to some implementations, the common electrode is for example formed by a shield plane or a shield surface located on a printed circuit board, PCB. In such implementations, the sense and the base electrode may for example be mechanically and/or electrically connected to the PCB.

According to some implementations, the sensor is implemented as an integrated circuit, for example as a microelectro-mechanical system, MEMS. In such implementations, the common electrode may for example be formed by a substrate of the integrated circuit, for example a semiconductor substrate.

According to some implementations, the common electrode is formed by a capacitor plate or a housing of the sensor or of a circuit arrangement comprising the sensor.

In some implementations, the common electrode is also used for shielding an interior of the sensor from external influences, for example for avoiding interferences with external electric fields.

According to some implementations, the sense and/or the base electrode are for example formed by or comprised by a substrate of the sensor and/or a housing of the sensor.

According to some implementations of the sensor circuit, the buffer element comprises a buffer operational amplifier with a first and a second buffer input and a buffer output. Therein, the first buffer input is connected to the sense electrode and the second buffer input is connected to the buffer output. The buffer output is connected to the common electrode. The first buffer input may for example be a non-inverting input, while the second buffer input may be an inverting input, or vice versa.

According to some implementations of the sensor circuit, the buffer element is adapted to drive the common electrode at a voltage applied to the sense electrode during the storing of the charge on the capacitive element and during reading out of the stored charge.

According to some implementations of the sensor circuit, the sense electrode is connected to a charge voltage via a first switch and the sensor circuit is adapted to close the first switch for storing the charge on the capacitive element. The sensor circuit is for example adapted to open the first switch for reading out the stored charge.

According to some implementations of the sensor circuit, the base electrode is connected to a first reference voltage via a second switch and the sensor circuit is adapted to close the second switch for storing the charge on the capacitive element. The sensor circuit is for example adapted to open the second switch for reading out the stored charge.

According to some implementations of the sensor circuit, the base electrode is connected to a second reference voltage via a third switch and the sensor circuit is adapted to close the third switch for reading out the stored charge. The sensor circuit is for example adapted to open the third switch for storing the charge on the capacitive element.

According to some implementations of the sensor circuit, the sensor circuit further comprises an integration unit with a first integration input coupled to the sense electrode for receiving a sense signal depending on the read out charge and adapted to generate, based on the sense signal at at least one integration output of the integration unit at least one output voltage being indicative of the stored charge.

According to some implementations of the sensor circuit, the sense electrode is connected to the integration unit via a fourth switch and the sensor circuit is adapted to close the fourth switch for reading out the stored charge. The sensor circuit is for example adapted to open the fourth switch for storing the charge on the capacitive element.

According to some implementations of the sensor circuit, the integration unit comprises a second integration input for example for receiving a reference signal.

In some implementations of the sensor circuit, the integration unit comprises a first and the second integration output. In such implementations, the integration unit is adapted to generate, based on the sense signal and/or the reference signal, a first output voltage at the first integration output and a second output voltage at the second integration output. An absolute value of the second output voltage may for example be equal to an absolute value of the first output voltage. In particular, a value of the second output voltage may be equal to an inverted value of the first output voltage.

According to some implementations of the sensor circuit, a value of the at least one output voltage is proportional to the stored charge.

According to some implementations of the sensor circuit, the integration unit comprises an operational amplifier connected between the first integration input and at least one integration output for generating the at least one output voltage. The integration unit further comprises a first integration capacitor connected between the first integration input and the at least one integration output.

In some implementations, the operational amplifier comprises a first output corresponding to or connected to the at least one integration output.

In some implementations, the operational amplifier comprises a first output and a second output corresponding to or connected to the first integration output and the second integration output, respectively. The first and the second output of the operational amplifier may for example be differential outputs. In particular, a signal generated at the second output of the operational amplifier may be inverted with respect to a signal generated as the first output of the operational amplifier. In some of such implementations, the first integration capacitor is connected between the first integration input and the first output of the operational amplifier. In some of such implementations, the integration unit further comprises a second integration capacitor connected between the first integration input and the second output of the operational amplifier.

According to some implementations of the sensor circuit, the sensor circuit further comprises a reference unit coupled between the first integration input and the least one reference terminal of the sensor circuit and configured to adjust the sense signal with respect to a reference value. In particular, the reference unit may be configured to adjust the sense signal by effectively subtracting the reference value from the sense signal.

According to some implementations of the sensor circuit, the reference unit comprises a first reference capacitor, switchably connected to the first integration input and switchably connected to the at least one reference terminal. Therein, a capacitance of the first reference capacitor is adjusted to a reference capacitance depending on the capacitive element.

In some implementations of the sensor circuit, the reference capacitance corresponds or approximately corresponds to a mean value of a capacitance of the capacitive element. The mean value may for example be a mean value between a minimum value and a maximum value of the capacitance of the capacitive element. Due to the dependence of the capacitance of the capacitive element on the quantity to be measured, the capacitance of the capacitive element may assume values between the minimum value and the maximum value. In some implementations, the capacitance of the capacitive element may also assume values larger than the maximum value and/or smaller than the minimum value. Then, capacitance values between the maximum value and to a minimum value may for example correspond to typical values for the capacitance of the capacitive element according to a respective application.

According to some implementations of the sensor circuit, the reference unit comprises a second reference capacitor switchably connected to the second integration input and switchably connected to the at least one reference terminal. According to some implementations, a capacitance of the second reference capacitor is equal or approximately equal to the capacitance of the first reference capacitor. According to other implementations, the capacitance of the second reference capacitor is equal or approximately equal to a multiple of the capacitance of the first reference capacitor.

According to some implementations of the sensor circuit, the reference unit comprises at least one further reference capacitor switchably connected to the first and/or the second integration input and switchably connected to the at least one reference terminal. According to some implementations, a capacitance of the at least one further reference capacitor is equal or approximately equal to the capacitance of the first and/or the second reference capacitor.

According to the improved concept, also a charge redistribution amplifier is provided. The charge redistribution amplifier comprises a sensor circuit according to the improved concept and is adapted to generate an output signal given by or based on the at least one output voltage.

According to the improved concept, also an integrator circuit is provided. The integrator circuit comprises a sensor circuit according to the improved concept and is adapted to generate an output signal given by or based on the at least one output voltage.

According to some implementations of the integrator circuit, the integrator circuit is implemented as a switched capacitor integrator circuit.

According to the improved concept, also a capacitance-to-digital converter, CDC, circuit is provided. The CDC circuit comprises a sensor circuit according to the improved concept, wherein the sensor is used as a sampling stage for the CDC circuit and the CDC circuit is adapted to generate a digital output signal based on the at least one output voltage.

According to some implementations of the CDC circuit, the CDC circuit comprises a sigma-delta-modulator adapted to generate the digital output signal or a signal based on which the CDC circuit generates the digital output signal.

According to some implementations of the CDC circuit, the sigma-delta-modulator is implemented as a first order sigma-delta-modulator, as a second order sigma-delta-modulator or as a higher-order sigma-delta-modulator.

According to some implementations of the CDC circuit, the sigma-delta-modulator comprises a first integrator, a quantizer and a first feedback circuit. The first integrator comprises the integration unit and is adapted to generate at least one integrated signal given by or based on the at least one output voltage. The quantizer is coupled to the at least one integration output and adapted to generate at least one quantized signal at a quantizer output depending on the at least one output voltage. The first feedback circuit is coupled between the quantizer output and the first integration input and is configured to subtract or effectively subtract a signal based on the at least one quantized signal from the sense signal.

According to some implementations of the CDC circuit, the first feedback circuit comprises a first feedback capacitor, being switchably connected to the first integration input. The first feedback capacitor is also switchably connected to the at least one reference voltage and switchably connected to a charge voltage. Therein, the charge voltage is applied to the sense terminal when storing the charge to the capacitive element.

According to some implementations of the CDC circuit, the first feedback circuit comprises a second feedback capacitor, switchably connected to the second integration input, switchably connected to the at least one reference voltage and switchably connected to a charge voltage. In some implementations, the first and the second reference capacitor have the same capacitance.

According to some implementations of the CDC circuit, the sigma-delta-modulator further comprises a filter coupled to the quantizer output and adapted to generate a filtered output signal based on the quantized signal.

According to some implementations, the filter is implemented as a digital filter, in particular as a digital low-pass filter.

According to some implementations of the CDC circuit, the CDC circuit further comprises a calibration unit coupled to an output of the filter and adapted to generate the digital output signal by calibrating and/or linearizing the filtered output signal.

In particular, the sensor may for example feature a non-linear signal output for example when the charge stored on the capacitive element is being read out. Then, the calibration unit may for example be configured to compensate such nonlinear signal output.

According to some implementations of the CDC circuit, the CDC circuit comprises a successive approximation CDC circuit and/or a successive approximation analog-to-digital converter circuit.

According to the improved concept, also a method for measuring a physical or chemical quantity is provided. The method comprises storing a charge on a capacitive element formed by a sense electrode and a base electrode of a capacitive sensor. The capacitive element has a capacitance depending on the physical or chemical quantity. A common electrode of the sensor forms a first parasitic capacitance together with the sense electrode and a second parasitic capacitance together with the base electrode. The method further comprises reading out the stored charge via the sense electrode and driving the common electrode to a voltage applied to the sense electrode at least during the reading out of the stored charge.

According to some implementations of the method, the common electrode surrounds at least a part of the sense electrode and/or the base electrode.

Further implementations of the method follow readily from the various implementations and embodiments of the sensor circuit, the charge distribution amplifier circuit, the integrator circuit and the CDC circuit, and vice versa.

BRIEF DESCRIPTION OF THE DRAWINGS

In the following, the improved concept is explained in detail with the aid of exemplary implementations by reference to the drawings. Components that are functionally identical or have an identical effect may be denoted by identical references. Identical components and/or components with identical effects may be described only with respect to the figure where they occur first; their description is not necessarily repeated in subsequent figures.

In the drawings.

DETAILED DESCRIPTION

Figure 1:
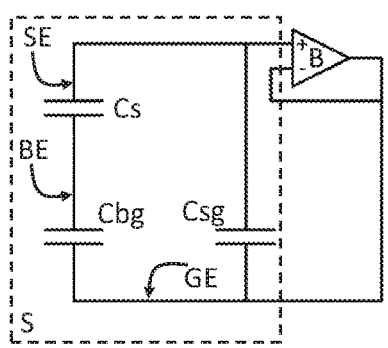
FIG. 1 shows a schematic representation of an exemplary implementation of a sensor circuit according to the improved concept.

FIG. 1 shows a schematic representation of an exemplary implementation of a sensor circuit according to the improved concept. The sensor circuit comprises a capacitive sensor S, which is represented in FIG. 1 by an equivalent circuit, and a buffer element B.

The sensor S comprises a sense electrode SE and a base electrode BE. The sense electrode SE and the base electrode BE together form a capacitive element Cs. In particular, the sense electrode SE and the base electrode BE may be not connected electrically with each other. The sensor S further comprises a common electrode GE that may for example surround the sense electrode SE and/or the base electrode BE at least partially. The common electrode GE may be not electrically connected to the base electrode BE nor to the sense electrode SE. However, the common electrode GE forms a first parasitic capacitance Csg together with the sense electrode SE and a second parasitic capacitance Cbg together with the base electrode BE.

The buffer element B may be implemented as an operational amplifier with a first buffer input, for example a non-inverting input, connected to the sense electrode SE and with a buffer output connected to the common electrode GE. Furthermore, the buffer element B may comprise a second buffer input, for example an inverting input, connected to the buffer output. By this arrangement, a voltage at the buffer output, that is at the common electrode GE, is driven at, particular is equal or approximately equal to, a voltage applied at the first buffer input, that is at the sense electrode SE.

The capacitive sensor S is sensitive to a physical or chemical quantity. To this end, a capacitance of the capacitive element Cs depends on the quantity. To measure the physical or chemical quantity, a charge may be stored by applying a charge voltage VA to the sense electrode SE and a first reference voltage VP to the base electrode BE. Then, the stored charge may be read out via the sense electrode SE, for example by connecting the sense electrode SE an integrating unit IU (not shown in FIG. 1, see FIGS. 3 and 4) and connecting the base electrode BE to a second reference voltage VN. Due to the continuous driving of the common electrode GE at the same voltage as the sense electrode SE, in particular during the reading out, the measurement is not affected by the parasitic capacitances Cbg, Csg. In particular, the base electrode BE is kept at the second reference voltage VN during the reading out.

The charge voltage VA may for example lie between the first and the second reference voltage VP, VN. The actual values of the voltages VA, VN, VP depend on the actual implementation. For example, the first reference VP voltage may lie between 1.7 V and 2 V. The second reference voltage VN may for example be zero and the charge voltage VA may for example lie between 0.85 V and 1 V. These numbers are only exemplary. Naturally, voltages with different values may be used.

During the frontend operation, for example during the reading out of the charge stored on the capacitive element Cs, a voltage applied at the sense electrode SE may change. Since the common electrode GE tracks the voltage applied at the sense electrode SE by being driven with the buffer element B, the charge stored on the parasitic capacitances Csg, Cbg may not change during the frontend operation. This avoids any charge being transferred between the parasitic capacitances Csg, Cbg and the capacitive element Cs. As a consequence, the correct charge stored on the capacitive element Cs may be sensed.

Depending for example on an application of the sensor circuit, in particular depending on the physical or chemical quantity to be measured, the implementation of the sensor S, in particular of the sense electrode SE, the base electrode BE and the common electrode GE may be different. For example, if the quantity corresponds to a pressure, at least one of the base electrode BE and the sense electrode SE may for example be movable. Then, upon a change in pressure, a distance between the base electrode BE and the sense electrode SE and consequently a capacitance of the capacitive element Cs may change.

Depending for example on the application and/or the implementation of the sensor, the common electrode GE may also be implemented in various ways. The common electrode may be implemented as a guard electrode and/or as a shield electrode. For example, the common electrode GE may be formed by a shield plane or a shield surface located on a printed circuit board, PCB. In such implementations, the sense and/or the base electrode SE, BE may for example be mechanically and/or electrically connected to the PCB. Alternatively, for example in implementations wherein the sensor is implemented as an integrated circuit, for example as a MEMS, the common electrode GE may for example be formed by a substrate of the integrated circuit, for example by a semiconductor substrate. Alternatively, the common electrode GE may be formed by a capacitor plate of the sensor S or of a circuit arrangement comprising the sensor S.

In some implementations, at least one of the sense electrode SE and the base electrode BE is implemented as a plate or a membrane. The common electrode GE may be implemented as a ring surrounding or partially surrounding said plate or membrane.

Alternatively or in addition, the common electrode may be arranged and adapted to achieve a particularly homogeneous electric field between the sense and the base electrode SE, BE.

Figure 2:
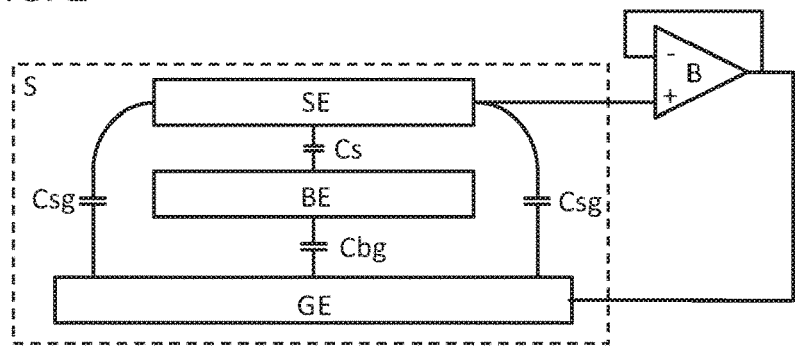
FIG. 2 shows a schematic representation of a further exemplary implementation of a sensor circuit according to the improved concept.

FIG. 2 shows a schematic representation of a further exemplary implementation of a sensor circuit according to the improved concept. The implementation of the sensor circuit is based on the implementation shown in FIG. 1. In particular, the equivalent circuit of the sensor S of FIG. 1 may represent the sensor S of the sensor circuit shown in FIG. 2.

In FIG. 2, the sense electrode SE, the base electrode BE and the common electrode GE are depicted as plates. However, the base electrode and/or the sense electrode may also be implemented differently, for example as a membrane. As explained for FIG. 1, the capacitive element Cs is formed by the sense electrode SE and the base electrode BE. The common electrode GE is in the example of FIG. 2 arranged below the sense and the base electrode SE, BE. In the shown example, a width of the common electrode GE is larger than a width of the sense and base electrodes SE, BE. Further, the electrodes SE, BE, GE are arranged symmetrically with respect to each other. Consequently, the first parasitic capacitance Csg is formed together with the sense electrode SE in equal parts by a part of the common electrode GE overlapping the sense and base electrode SE, BE on a first side and by a part of the common electrode GE overlapping the sense and base electrode SE, BE on a second side being opposite to the first side. In particular, each of said parts may contribute equally to a value of the first parasitic capacity Csg. Furthermore, the second parasitic capacitance Cbg is formed by the common electrode GE together with the base electrode BE.

Figure 3:
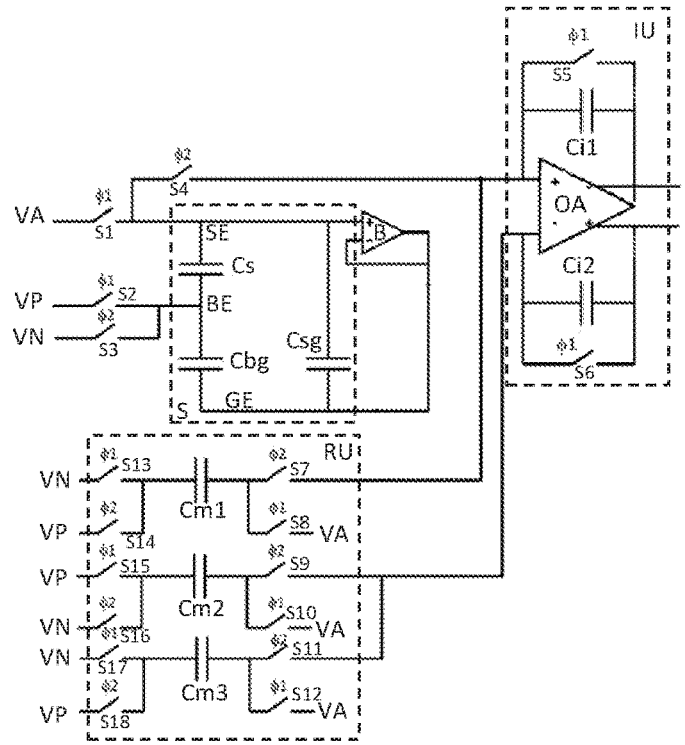
FIG. 3 shows a further exemplary implementation of a sensor circuit according to the improved concept.

FIG. 3 shows a further exemplary implementation of a sensor circuit according to the improved concept. In particular, the sensor circuit shown in FIG. 3 may represent or be part of a charge redistribution amplifier according to the improved concept.

The sensor circuit of FIG. 3 is based on the sensor circuit of FIG. 1. In addition, the sense electrode SE is connected to a charge voltage VA via a switch S1. The base electrode BE is connected to a first reference voltage VP via a switch S2 and to a second reference voltage VN via a switch S3. The sensor circuit also comprises an integration unit IU and a reference unit RU. The integration unit IU comprises a first integration input connected to the sense electrode SE via a switch S4 and to the reference unit RU and a second integration input connected to the reference unit RU.

Furthermore, the integration unit IU comprises an operational amplifier OA with a non-inverting input connected to the first integration input, an inverting input connected to the second integration input, an inverting output connect to the first integration output and a non-inverting output connected to the second integration output. The integration unit IU comprises a first integration capacitor Ci1 connected between the first integration input and the first integration output and a second integration capacitor Ci2 connected between the second integration input and the second integration output. Moreover, the integration unit IU comprises switches S5, S6 for shorting the first and the second integration capacitor Ci1, Ci2.

The reference unit RU comprises a first reference capacitor Cm1 with a first plate connected to the first integration input via a switch S7 and to the charge voltage VA via a switch S8. A second plate of the first reference capacitor Cm1 is connected to the first reference voltage VP via a switch S14 and to the second reference voltage VN via a switch S13. The reference unit RU comprises a second reference capacitor Cm2 with a first plate connected to the second integration input via a switch S9 and to the charge voltage VA via a switch S10. A second plate of the second reference capacitor Cm2 is connected to the first reference voltage VP via a switch S15 and to the second reference voltage VN via a switch S16. The reference unit RU comprises a third reference capacitor Cm3 with a first plate connected to the second integration input via a switch S11 and to the charge voltage VA via a switch S12. A second plate of the second reference capacitor Cm2 is connected to the first reference voltage VP via a switch S18 and to the second reference voltage VN via a switch S17.

The switches S1, S2, S5, S6, S8, S10, S12, S13, S15, S17 may be controlled by a first switch signal Φ1, in particular may be closed if the first switch signal Φ1 is logic high and opened if the first switch signal Φ1 is logic low. On the other hand, the switches S3, S7, S9, S11, S14, S16, S18 may be controlled by a second switch signal Φ2, in particular may be closed if the second switch signal Φ2 is logic high and opened if the second switch signal Φ2 is logic low.

Figure 6:
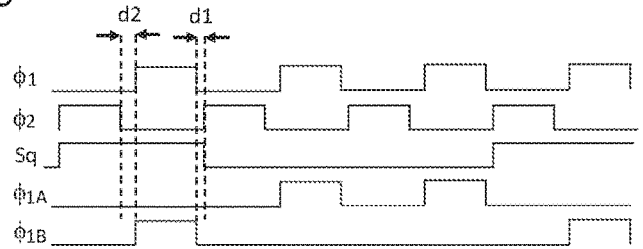
FIG. 6 shows a timing diagram of signals within an exemplary implementation capacitance-to-digital converter circuit according to the improved concept and/or a sensor circuit according to the improved concept.

For a timing of the first and the second switch signal Φ1, Φ2, it is referred to FIG. 6. In particular, the first and the second switch signal Φ1, Φ2 may for example not be logic high at the same time.

In operation, when the first switch signal Φ1 is logic high, the sense electrode SE is connected to the charge voltage VA and the base electrode BE is connected to the first reference voltage VP for storing a charge on to the capacitive element Cs. The amount of charge stored depends on the capacity of the capacitive element Cs, and therefore on the physical or chemical quantity to be measured. Then, when the second switch signal Φ2 is logic high, the base electrode BE is connected to the second reference voltage VN and the sense electrode SE is connected to the first integration input. Therefore, a sense signal corresponding to the charge stored on the capacitive element Cs is applied to the first integration input. Consequently, the integration unit IU, in particular the operational amplifier OA, generates a first output voltage at the first integration output and a second output voltage at the second integration output depending on the sense signal. The first and the second output voltage depend on the charge stored on the capacitive element Cs, and therefore on the physical or chemical quantity to be measured.

During the second switch signal Φ2 being logic high, a voltage applied at the sense electrode SE may vary. However, due to the coupling of the buffer element B between the sense electrode SE and the common electrode GE, the same or approximately the same voltage is permanently applied to the sense electrode SE and the common electrode GE. Furthermore, the base electrode BE is constantly kept at the second reference voltage VN during this period. Consequently, charges stored on the first and second parasitic capacitances Csg, Cbg do not change during the read out of the charge stored on the capacitive element Cs via the sense electrode SE. Therefore, the sense signal, and in consequence also the first and the second output voltage, do not depend on the parasitic capacitances Csg, Cbg but only on the capacitance of the capacitive element Cs. Therefore, the physical or chemical quantity may be measured with a particularly high accuracy.

The capacitance of the reference capacitors Cm1, Cm2, Cm3 is for example adjusted to a reference capacitance. In particular, the reference capacitance may correspond to a mean value of the capacitance of the capacitive element Cs. For example, depending on the physical or chemical quantity to be measured, the capacitance of the capacitive element Cs may lie between a minimum value and a maximum value of the capacitance. Then, the capacitance of the reference capacitors Cm1, Cm2, Cm3 may be a mean value of the minimal value and the maximum value.

Due to the described connection and switching of the reference unit RU, the sense signal is adjusted with respect to a reference value corresponding to the reference capacitance, that is for example to the mean value of the capacitance of the capacitive element Cs.

The first and the second integration capacitor Ci1, Ci2 may for example be shorted by means of the first switch signal Φ1 every time charge is being stored on the capacitive element Cs.

Figure 4:
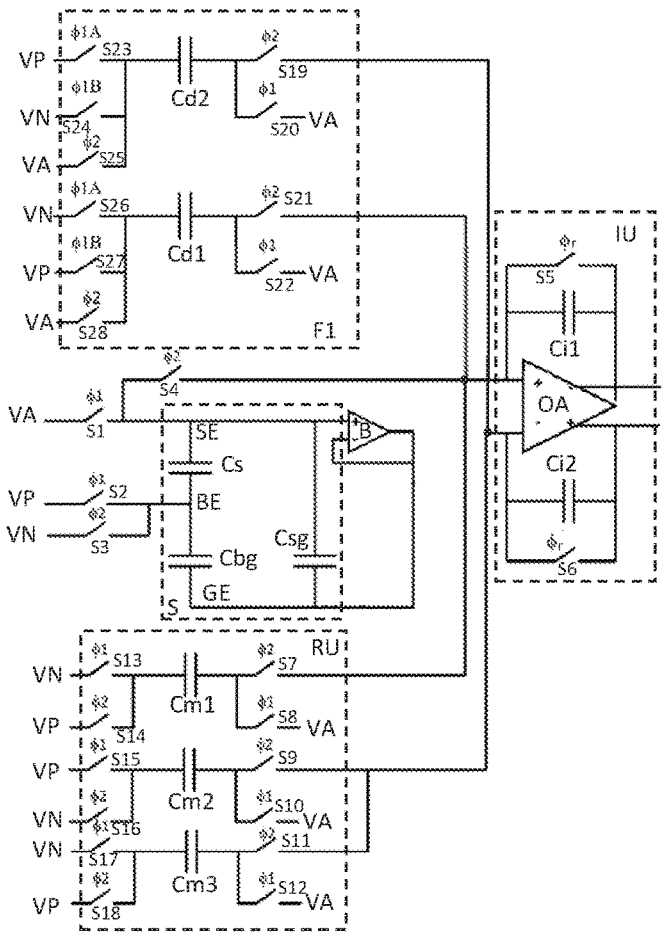
FIG. 4 shows a further exemplary implementation of a sensor circuit according to the improved concept.

FIG. 4 shows a further exemplary implementation of a sensor circuit according to the improved concept. The sensor circuit of FIG. 4 is based on the sensor circuit shown in FIG. 3.

In addition, the sensor circuit of FIG. 4 comprises a first feedback circuit F1 connected to the first and the second integration input. The first feedback circuit F1 comprises a first feedback capacitor Cd1 with a first plate connected to the first integration input via a switch S21 and to the charge voltage VA via a switch S22. A second plate of the first feedback capacitor Cd1 is connected to the first reference voltage VP via a switch S27, to the second reference voltage VN via a switch S26 and to the charge voltage VA via a switch S28. The first feedback circuit F1 comprises a second feedback capacitor Cd2 with a first plate connected to the second integration input via a switch S19 and to the charge voltage VA via a switch S20. A second plate of the second feedback capacitor Cd2 is connected to the first reference voltage VP via a switch S23, to the second reference voltage VN via a switch S24 and to the charge voltage VA via a switch S25.

The switches S20 and S22 may be controlled by the first switch signal Φ1, in particular may be closed if the first switch signal Φ1 is logic high and opened if the first switch signal Φ1 is logic low. The switches S19, S21, S25, S28 may be controlled by the second switch signal Φ2, in particular may be closed if the second switch signal Φ2 is logic high and opened if the second switch signal Φ2 is logic low. The switches S23 and S26 may be controlled by a first feedback signal Φ1A, in particular may be closed if the first feedback signal Φ1A is logic high and opened if the first feedback signal Φ1A is logic low. The switches S24 and S27 may be controlled by a second feedback signal Φ1B, in particular may be closed if the second feedback signal Φ1B is logic high and opened if the second feedback Φ1B is logic low.

For a timing of the first and the second feedback signal Φ1A, Φ1B, it is referred to FIG. 6.

In FIG. 4, the first and the second integration capacitor Ci1, Ci2 may be controlled by a reset signal Φr for example instead of being controlled by the first switch signal Φ1 as shown in FIG. 3. The sensor circuit shown in FIG. 4 may for example represent or be part of an integrator circuit according to the improved concept. The sensor circuit of FIG. 4 may for example be part of an integrator, in particular a first integrator, of a capacitance-to-digital converter, CDC, circuit and/or a sigma-delta-modulator. The reset signal Φr may for example be logic high to short the first and the second integration capacitor Ci1, Ci2 at specified instances of operation of the sensor circuit.

By means of the first feedback circuit F1, the sensor circuit may effectively subtract a signal from the sense signal. The signal subtracted from the sense signal may for example be generated from another component of the integrator circuit, the CDC circuit and/or the sigma-delta-modulator. It is referred to FIG. 5 for a more detailed description.

Figure 5:
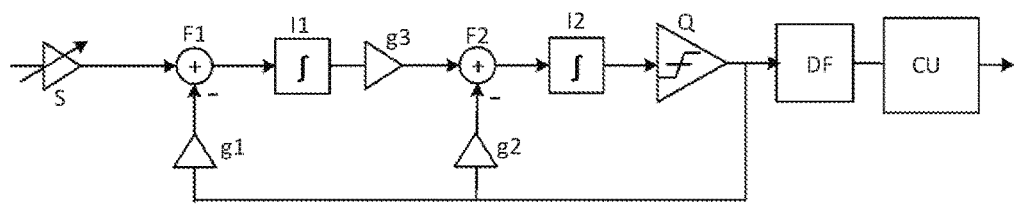
FIG. 5 shows an exemplary implementation of a capacitance-to-digital converter circuit according to the improved concept.

FIG. 5 shows an exemplary implementation of a capacitance-to-digital converter, CDC, circuit according to the improved concept.

The CDC circuit comprises a sensor circuit according to the improved concept. For the sake of clarity, only the sensor S and the first feedback circuit F1 are shown in FIG. 5, while the buffer element B, though being connected between the sense electrode SE and the common electrode GE as described in FIGS. 1 to 4, is not shown in FIG. 5. In particular, the sensor circuit is implemented as shown in FIG. 4. The CDC circuit comprises a first integrator I1, comprising the integration unit IU of the sensor circuit. The CDC circuit further comprises a second integrator I2 connected to an output of the first integrator I1 and a second feedback circuit F2 connected between the first and the second integrator I1, I2. The second feedback circuit F2 may for example be implemented analogously to the first feedback circuit F1. The CDC circuit further comprises a quantizer Q connected to an output of the second integrator I2, a filter DF connected to an output of the quantizer Q and the calibration unit CU connected to an output of the filter DF. The filter DF may for example be implemented as a digital filter, in particular as a digital low-pass filter. Furthermore, the output of the quantizer Q is also connected to the first and second feedback circuit F1, F2.

Furthermore, weighting factors g1, g2, g3 are indicated between the first feedback circuit F1 and the quantizer Q, between the second feedback circuit F2 and the quantizer Q and between the first integrator I1 and the second feedback circuit F2, respectively. The weighting factors g1, g2, g3 may for example depend on capacitance values of the sensor circuit, for example on the capacitances of the capacitive element Cs, the reference capacitors Cm1, Cm2, Cm3, and/or the integration capacitors Ci1, Ci2. For example, the first weighting factor g1 may represent a weight given by (cs−cm)/ci, wherein cs represents the capacitance of the capacitive element Cs, cm represents the capacitance of each of the reference capacitors Cm1, Cm2, Cm3 and ci represents the capacitance of each of the integration capacitors Ci1, Ci2. The second and the third weighting factor g2, g3 may be given by analog expressions.

In operation, the sensor S is used as a sampling stage for the CDC circuit. That is, charge is stored on the capacitive element Cs and read out via the sense electrode SE, as described with respect to the previous figures. In particular, the common electrode GE is continuously driven at the same voltage as applied to the sense electrode SE, at least during the reading out of the charge, as described previously. The first integrator I1 generates a first integrated signal based on the first and the second output voltage of the sensor circuit. Therein, the sense signal generated by the sensor circuit by reading out the charge may be adjusted by means of the first feedback circuit F1 as described before.

Then, the first integrated signal is weighted by means of the third weighting factor g3 and adjusted by means of the second feedback circuit F2 analogously as described with respect to the first feedback circuit F1. The weighted and adjusted first integration signal is fed to the second integrator I2, which generates a second integrated signal based thereupon. The second integrated signal is fed to the quantizer Q, which generates a quantized signal Sq based on the second integrated signal, and therefore also based on the first integrated signal and the first and second output voltage of the sensor circuit, respectively.

The quantized signal Sq is correspondingly weighted by the first and the second weighting factor g1, g2 is then fed back to the first and the second feedback circuit F1, F2, respectively. The quantized signal Sq is also fed to the filter DF, which generates a filtered output signal based thereupon. The filtered output signal is fed to the calibration unit CU, which generates a digital output signal by calibrating and/or linearizing the filtered output signal. An output bit stream corresponding to the digital output signal is indicative and/or may be proportional to the physical or chemical quantity to be measured.

The first and the second feedback signal Φ1A, Φ1B may for example be generated based on the quantized signal Sq, as explained with respect to FIG. 6.

FIG. 6 shows a timing diagram of signals within an exemplary implementation capacitance-to-digital converter circuit according to the improved concept. In particular, the signals shown in FIG. 6 may correspond to the respective figures occurring in the implementations of the sensor circuit and/or the CDC circuit of FIGS. 3 to 5.

FIG. 6 schematically shows the first and the second switch signal Φ1, Φ2, the quantized signal Sq, as well as the first and the second feedback signal Φ1A, Φ1B as a function of time. The first switch signal Φ1 may for example be derived from a clock signal and may feature specified periods of logic high and specified periods of logic low. In the shown example, the periods of logic high of the first switch signal Φ1 are for example shorter than the periods of logic low of the first switch signal. The second switch signal Φ2 may for example always be logic low whenever the first switch signal Φ1 is logic high and may be logic low only during periods when the first signal Φ1 is logic low. In particular, every falling edge of the first switch signal Φ1 may be followed by a rising edge of the second switch signal Φ2 after a first delay d1 and every falling edge of the second switch signal Φ2 may be followed by a rising edge of the first switch signal Φ1 after a second delay d2.

The first feedback signal Φ1A may for example correspond to the first switch signal Φ1 whenever the quantized signal Sq is logic low and be logic low otherwise. The second feedback signal Φ1B may for example correspond to the first switch signal Φ1 whenever the quantized signal Sq is logic high and be logic low otherwise.

According to the improved concept, a charge transfer between the capacitive element Cs and the parasitic capacitances Csg, Cbg is suppressed by driving the common electrode GE of the capacitive sensor frontend to the same voltage as the sense electrode SE. In this way, repeated measurements can be avoided, an improved accuracy and processing speed as well as a decreased power consumption may be achieved.

The improved concept may also be employed for measuring the capacitance of an external capacitor component, which has a capacitance that does not necessarily depend on a physical or chemical quantity. Then, the capacitor plates of the external capacitor component correspond to the sense and base electrode, respectively.

The invention claimed is:

1. A sensor circuit for measuring a physical or chemical quantity, comprising
    a capacitive sensor, comprising
        a sense electrode and a base electrode together forming a capacitive element with a capacitance depending on the quantity;
        a common electrode forming a first parasitic capacitance together with the sense electrode and a second parasitic capacitance together with the base electrode; wherein the sensor circuit is adapted to store a charge on the capacitive element via the sense electrode and the base electrode and to read out the stored charge via the sense electrode;
    a buffer element connected between the sense electrode and the common electrode and adapted to drive the common electrode at a voltage applied to the sense electrode at least during the reading out of the stored charge;
    an integration unit with a first integration input coupled to the sense electrode for receiving a sense signal depending on the read out charge and adapted to generate, based on the sense signal, at at least one integration output of the integration unit at least one output voltage being indicative of the stored charge; and
    a reference unit coupled between the first integration input and at least one reference terminal of the sensor circuit and configured to adjust the sense signal with respect to a reference value.

2. The sensor circuit according to claim 1, wherein the buffer element is adapted to drive the common electrode at a voltage applied to the sense electrode during the storing of the charge on the capacitive element and during reading out of the stored charge.

3. The sensor circuit according to claim 1, wherein the sense electrode is connected to a charge voltage via a first switch and the sensor circuit is adapted to close the first switch for storing the charge on the capacitive element.

4. The sensor circuit according to claim 1, wherein the base electrode is connected to a first reference voltage via a second switch and the sensor circuit is adapted to close the second switch for storing the charge on the capacitive element.

5. The sensor circuit according to claim 1, wherein the base electrode is connected to a second reference voltage via a third switch and the sensor circuit is adapted to close the third switch for reading out the stored charge.

6. The sensor circuit according to claim 1, wherein the sense electrode is connected to the integration unit via a fourth switch and the sensor circuit is adapted to close the fourth switch for reading out the stored charge.

7. The sensor circuit according to claim 1, wherein a value of the at least one output voltage is proportional to the stored charge.

8. The sensor circuit according to claim 1, wherein the integration unit comprises
    an operational amplifier connected between the first integration input and the at least one integration output for generating the at least one output voltage; and
    a first integration capacitor connected between the first integration input and the at least one integration output.

9. The sensor circuit according to claim 1, wherein the reference unit comprises a first reference capacitor, switchably connected to the first integration input and switchably connected to the at least one reference terminal, wherein a capacitance of the first reference capacitor is adjusted to a reference capacitance depending on the capacitive element.

10. A charge redistribution amplifier circuit comprising a sensor circuit according to claim 1, wherein the charge redistribution amplifier circuit is adapted to generate an output signal given by or based on the at least one output voltage.

11. An integrator circuit comprising a sensor circuit according to claim 1, wherein the integrator circuit is adapted to generate an output signal given by or based on the at least one output voltage.

12. The integrator circuit according to claim 11, wherein the integrator circuit is implemented as a switched capacitor integrator circuit.

13. A capacitance-to-digital converter, CDC, circuit comprising a sensor circuit according to claim 1, wherein the sensor is used as a sampling stage for the CDC circuit and the CDC circuit is adapted to generate a digital output signal based on the at least one output voltage.

14. The capacitance-to-digital converter circuit according to claim 13 comprising a sigma-delta-modulator adapted to generate the digital output signal or a signal based on which the CDC circuit generates the digital output signal.

15. The capacitance-to-digital converter circuit according to claim 14, wherein the sigma-delta-modulator comprises
    a first integrator comprising the integration unit and adapted to generate at least one integrated signal given by or based on the at least one output voltage;
    a quantizer coupled to the at least one integration output and adapted to generate at least one quantized signal at a quantizer output depending on the at least one output voltage; and
    a first feedback circuit coupled between the quantizer output and the first integration input and configured to subtract a signal based on the least one quantized signal from the sense signal.

16. The capacitance-to-digital converter circuit according to claim 15, wherein the sigma-delta-modulator further comprises a filter coupled to the quantizer output and adapted to generate a filtered output signal based on the quantized signal.

17. The capacitance-to-digital converter circuit according to claim 16, further comprising a calibration unit coupled to an output of the filter and adapted to generate the digital output signal by calibrating and/or linearizing the filtered output signal.

18. A method for measuring a physical or chemical quantity, wherein the method comprises
    storing a charge on a capacitive element formed by a sense electrode and a base electrode of a capacitive sensor and having a capacitance depending on the quantity, wherein a common electrode of the sensor forms a first parasitic capacitance together with the sense electrode and a second parasitic capacitance together with the base electrode;

reading out the stored charge via the sense electrode;

driving the common electrode at a voltage applied to the sense electrode at least during the reading out of the stored charge;

receiving a sense signal depending on the read out charge and generating by an integration unit, based on the sense signal, at least one output voltage being indicative of the stored charge; and adjusting the sense signal with respect to a reference value.

* * * * *